(12) United States Patent
Nilsson et al.

(10) Patent No.: US 11,969,529 B2
(45) Date of Patent: Apr. 30, 2024

(54) PATIENT AND TREATMENT RECORDS

(71) Applicant: GAMBRO LUNDIA AB, Lund (SE)

(72) Inventors: Roger Nilsson, Hoor (SE); Roland Persson, Limhamn (SE); Bendik Torvin, Schaanwald (LI)

(73) Assignee: Gambro Lundia AB, Lund (SE)

( * ) Notice: Subject to any disclaimer, the term of this patent is extended or adjusted under 35 U.S.C. 154(b) by 1197 days.

(21) Appl. No.: 16/464,959

(22) PCT Filed: Nov. 22, 2017

(86) PCT No.: PCT/EP2017/080067
§ 371 (c)(1),
(2) Date: May 29, 2019

(87) PCT Pub. No.: WO2018/099785
PCT Pub. Date: Jun. 7, 2018

(65) Prior Publication Data
US 2019/0328950 A1    Oct. 31, 2019

(30) Foreign Application Priority Data

Nov. 29, 2016  (SE) .................................. 1651568-6

(51) Int. Cl.
*A61M 1/16* (2006.01)
*A61M 1/14* (2006.01)
(Continued)

(52) U.S. Cl.
CPC .......... *A61M 1/1605* (2014.02); *A61M 1/152* (2022.05); *A61M 1/154* (2022.05);
(Continued)

(58) Field of Classification Search
CPC .. A61M 1/1605; A61M 1/267; A61M 1/3431; A61M 1/3437; A61M 1/1654;
(Continued)

(56) References Cited

U.S. PATENT DOCUMENTS

| 5,776,345 A | 7/1998 | Truitt |
| 2005/0102165 A1* | 5/2005 | Oshita .................... G16H 10/40 |
| | | 705/3 |

(Continued)

FOREIGN PATENT DOCUMENTS

| EP | 2883557 | 6/2015 | |
| EP | 2883557 A1 * | 6/2015 | .......... A61M 1/1601 |

(Continued)

OTHER PUBLICATIONS

PCT Search Report and Written Opinion for PCT/EP2017/080067 dated Jan. 8, 2018 (9 pages).

*Primary Examiner* — Philip R Wiest
(74) *Attorney, Agent, or Firm* — Mueting Raasch Group

(57) ABSTRACT

The exemplary systems and methods may generate treatment records for extracorporeal blood treatments. The treatment records may include a plurality of values of various parameters. The various parameters may include a compulsory set of parameters that are preset, a dependent set of parameters that a dependent on one or more of a selected treatment and a system configuration, and a discretionary set of parameters that are selected by a user.

69 Claims, 8 Drawing Sheets

(51) Int. Cl.
  *A61M 1/26* (2006.01)
  *A61M 1/34* (2006.01)
  *A61M 1/36* (2006.01)

(52) U.S. Cl.
  CPC .......... *A61M 1/155* (2022.05); *A61M 1/1654* (2013.01); *A61M 1/267* (2014.02); *A61M 1/3413* (2013.01); *A61M 1/3431* (2014.02); *A61M 1/3437* (2014.02); *A61M 1/36222* (2022.05); *A61M 1/36224* (2022.05); *A61M 1/36225* (2022.05); *A61M 2202/0478* (2013.01); *A61M 2202/0498* (2013.01); *A61M 2205/3317* (2013.01); *A61M 2205/3334* (2013.01); *A61M 2205/3368* (2013.01); *A61M 2205/505* (2013.01); *A61M 2205/6072* (2013.01); *A61M 2230/30* (2013.01)

(58) Field of Classification Search
  CPC ........ A61M 1/3413; A61M 2202/0478; A61M 2202/0498; A61M 2205/3317; A61M 2205/3334; A61M 2205/3368; A61M 2205/505; A61M 2205/6071; A61M 2230/30; G16H 50/00; G16H 50/20
  See application file for complete search history.

(56) References Cited

U.S. PATENT DOCUMENTS

| | | | |
|---|---|---|---|
| 2009/0095679 | A1 | 4/2009 | Demers |
| 2011/0077574 | A1* | 3/2011 | Sigg .................. A61M 1/3403 604/6.01 |
| 2012/0138533 | A1 | 6/2012 | Curtis |
| 2013/0190717 | A1* | 7/2013 | Dollar .................. A61M 5/172 434/262 |
| 2013/0274642 | A1* | 10/2013 | Soykan ................ A61B 5/4848 604/5.01 |
| 2013/0297330 | A1* | 11/2013 | Kamen .................. G16H 40/60 705/2 |
| 2015/0196699 | A9 | 7/2015 | Wilt |
| 2016/0303303 | A1 | 10/2016 | Rovatti |

FOREIGN PATENT DOCUMENTS

| | | |
|---|---|---|
| EP | 2597584 | 1/2019 |
| JP | 2007/029705 | 2/2007 |
| JP | 2015/062695 | 4/2015 |
| WO | WO 2010/027437 | 3/2010 |
| WO | WO 2013/040182 | 3/2013 |
| WO | WO 2014/105517 | 7/2014 |

* cited by examiner

Treatment Record

Patient name: Jack Johanssen
Patient ID: 123
Clinic name: ABC Clinic
Machine name: XYZ Machine Date: 2016 July 30
Treatment start: 13:36
Treatment type: HD

| Time | QB | QB Acc | VP | AP | UF Acc | UFR | QD | Na+ | HCO3 | BP SYS | BP DIA | BP Pulse | K | KT/V | TMP | Temp |
|---|---|---|---|---|---|---|---|---|---|---|---|---|---|---|---|---|
| Pre treatment | | | | | | | | | | 120 | 90 | 75 | | | | |
| 3:55 | 270 | 1.35 | 110 | -85 | 0.08 | 1.0 | 600 | 138 | 32 | | | | 250 | 0.2 | 32 | 37 |
| 3:30 | 280 | 8.35 | 115 | -86 | 0.5 | 1.0 | 600 | 138 | 32 | | | | 260 | 0.6 | 32 | 37 |
| 2:55 | | | | | | | | | | 125 | 88 | 69 | | | | |
| 3:00 | 275 | 16.6 | 120 | -88 | 1.0 | 1.0 | 600 | 138 | 32 | | | | 257 | 0.7 | 32 | 37 |
| 2:30 | 280 | 25 | 125 | -86 | 1.5 | 1.0 | 600 | 138 | 32 | | | | 255 | 0.75 | 32 | 37 |
| 2:15 | | | | | | | | | | 122 | 87 | 73 | | | | |
| 2:00 | 270 | 33.1 | 125 | -85 | 2.0 | 1.0 | 600 | 138 | 32 | | | | 253 | 0.8 | 32 | 37 |
| 1:30 | 275 | 41.35 | 130 | -90 | 2.5 | 1.0 | 600 | 138 | 32 | | | | 252 | 0.9 | 32 | 37 |
| 1:25 | | | | | | | | | | 134 | 92 | 75 | | | | |
| 1:00 | 275 | 49.6 | 135 | -92 | 3.0 | 1.0 | 600 | 138 | 32 | | | | 250 | 1.1 | 32 | 37 |
| 0:30 | 275 | 57.85 | 140 | -92 | 3.5 | 1.0 | 600 | 138 | 32 | | | | 251 | 1.3 | 32 | 37 |
| 0:05 | 280 | 64.85 | 150 | -93 | 3.92 | 1.0 | 600 | 138 | 32 | | | | 252 | 1.4 | 32 | 37 |
| Post treatment | | | | | | | | | | 135 | 88 | 80 | | | | |

Access type: DN
Treatment time: 4:00
UF Volume: 4.0
Heparin: Bolus

Notes: Patient hypertension after 2:30, gave saline bolus

Signature: ..................................

Fig. 4

PATIENT AND TREATMENT RECORDS

This application is a U.S. National Stage Application of International Application No. PCT/EP2017/080067 filed 22 Nov. 2017 and published in English on 7 Jun. 2018 as International Publication No. WO 2018/099785 A1, which claims the benefit of priority under 35 U.S.C. § 119(a) of Swedish Patent Application No. 1651568-6 filed 29 Nov. 2016, each of which are incorporated herein by reference in their entireties.

The disclosure herein relates to medical treatment systems. More particularly, the disclosure relates to providing and generating patient and treatment records related to extracorporeal blood treatments performed by extracorporeal blood treatment systems.

Medical treatment clinics may create patient and treatment records for medical treatments performed in the clinic. The treatment records may include various parameters of each treatment and may be created by a user such as a nurse manually recording such parameters onto sheet of paper (e.g., a form). The user may periodically visit each patient undergoing a treatment to record the present values of the various parameters onto the treatment record. Upon the end of a treatment, the user may sign the treatment record.

Medical treatment systems may be configured to perform extracorporeal blood treatment using extracorporeal blood treatment apparatus. Extracorporeal blood treatment may refer to taking blood from a patient, treating the blood outside the patient, and returning the treated blood to the patient. Extracorporeal blood treatment is typically used to extract undesirable matter or molecules from the patient's blood, and/or to add beneficial matter or molecules to the blood. Extracorporeal blood treatment may be used with patients incapable of effectively eliminating such undesirable matter from their blood, for example, in the case of a patient who is suffering from temporary or permanent kidney failure. These and other patients may, for instance, undergo extracorporeal blood treatment to add to or to eliminate matter from their blood, to maintain an acid-base balance, and/or to eliminate excess body fluids.

SUMMARY

The exemplary systems and methods may be described as overcoming usability barriers to creating accurate treatment records and offering a user-friendly graphical user interface to assist users in generating and storing such treatment records. For example, the exemplary systems and methods may be described as automatically generating a treatment record without requiring users to periodically, manually record treatment parameters on a treatment record. Further, the exemplary systems and methods may be described as resulting in a unique and user-friendly way to generate and store treatment records. Additionally, the display of the treatment records on a graphical user interface may provide user-friendly accessibility to the recorded values of various parameters measured, or monitored, during the treatment cycle.

It may be further described that the exemplary systems and methods may make handling treatment records easy to understand, intuitive to operate, and welcoming to users. Further, the exemplary systems and methods may be described as providing, or giving, users clear, consistent processes for the generation and storage of treatment records, which may reduce stress and improve patient safety, work flow, and efficiency. The exemplary systems and methods may translate to a better, more efficient working environment for users, which may thereby provide a safer and better treatment experience for patients. Additionally, the exemplary systems and methods may improve patient adherence by providing a more pleasant experience.

One exemplary extracorporeal blood treatment system may include extracorporeal blood treatment apparatus, a display including a graphical user interface, and a computing apparatus including one or more processors and operatively coupled to the extracorporeal blood treatment apparatus and the display. The extracorporeal blood treatment apparatus may include one or more pumps, one or more sensors, and one or more disposable elements for use in a plurality of different extracorporeal blood treatment modalities. The graphical user interface may be configured to display treatment records for an extracorporeal blood treatment. The computing apparatus may be configured to select an extracorporeal blood treatment modality from the plurality of different extracorporeal blood treatment modalities in response to the user using the graphical user interface, perform the extracorporeal blood treatment according to the selected extracorporeal blood treatment modality for a patient using the extracorporeal blood treatment apparatus, monitor a plurality of parameters using the extracorporeal blood treatment apparatus during the extracorporeal blood treatment, generate a treatment record, and display the treatment record on the graphical user interface in response to the end of the extracorporeal blood treatment.

One exemplary method for an extracorporeal blood treatment system may include providing extracorporeal blood treatment apparatus including one or more pumps, one or more sensors, and one or more disposable elements for use in performing an extracorporeal blood treatment. The exemplary method may further include selecting an extracorporeal blood treatment modality from the plurality of different extracorporeal blood treatment modalities, performing the extracorporeal blood treatment according to the selected extracorporeal blood treatment modality for a patient using the extracorporeal blood treatment apparatus, monitoring a plurality of parameters using the extracorporeal blood treatment apparatus during the extracorporeal blood treatment, generating a treatment record, and displaying the treatment record on a graphical user interface in response to the end of the extracorporeal blood treatment.

The exemplary treatment record generated by the exemplary systems and methods described herein may include patient and treatment information, the selected extracorporeal blood treatment modality, a plurality of values for a compulsory set of the plurality of parameters monitored during the selected extracorporeal blood treatment, a plurality of values for a dependent set of the plurality of parameters monitored during the selected extracorporeal blood treatment, and/or a plurality of values for a discretionary set of the plurality of parameters monitored during the extracorporeal blood treatment. The compulsory set of the plurality of parameters may not be set by a user. The dependent set of the plurality of parameters may be selected in response to at least the selection of the extracorporeal blood treatment modality from the plurality of different extracorporeal blood treatment modalities. The discretionary set of the plurality of parameters may be selectable by a user.

In one or more embodiments, the computing apparatus may be further configured to execute or the method may further include allowing a user to disregard the displayed treatment record and deleting the treatment record in response to the user disregarding the displayed treatment record after a selected time period elapses.

In one or more embodiments, the treatment record may further include a selectable print graphical area, and the computing apparatus may be further configured to execute or the method may further include allowing a user to select the selectable print graphical area to print the treatment record using a printer and deleting the treatment record in response to the user selecting the selectable print graphical area to print the treatment record using a printer.

In one or more embodiments, the treatment record may further include a selectable transfer graphical area, and the computing apparatus may be further configured to execute or the method may further include allowing a user to select the selectable transfer graphical area to transfer the treatment record to another device and deleting the treatment record in response to the user selecting the selectable transfer graphical area to transfer the treatment record to another device.

In one or more embodiments, the plurality of parameters may be monitored periodically using the extracorporeal blood treatment apparatus during the extracorporeal blood treatment, and the plurality of values of the compulsory set of the plurality of parameters, the plurality of values of the dependent set of the plurality of parameters, and the plurality of values of the discretionary set of the plurality of parameters may be numerically depicted in the treatment record.

In one or more embodiments, the dependent set of the plurality of parameters may be selected in response to at least the configuration of the extracorporeal blood treatment system.

In one or more embodiments, the plurality of different extracorporeal blood treatment modalities may include at least two of hemodialysis, hemodiafiltration predilution, hemodiafiltration postdilution, and hemofiltration.

In one or more embodiments, the patient and treatment information may include one or more of patient name, patient identifier, system identifier, and clinic name.

In one or more embodiments, the compulsory set of the plurality of parameters may include one or more of blood flow rate, accumulated blood flow rate, venous pressure, arterial pressure, accumulated ultrafiltration volume, dialysate flow rate, dialysate sodium concentration, and dialysate bicarbonate concentration.

In one or more embodiments, the dependent set of the plurality of parameters may include one or more of systolic blood pressure, diastolic blood pressure, pressure pulse, accumulated heparin volume, dialyzer clearance of urea, dialyzer clearance of urea multiplied by time divided by volume of distribution of urea (KT/V), dialyzer clearance of urea multiplied by time (KT), relative blood volume percentage, convective volume, and convective clearance rate. Further, in one or more embodiments, the convective volume and the convective clearance rate may be selected to be within the dependent set of the plurality of parameters in response to the selection of hemofiltration or hemodiafiltration from the plurality of different extracorporeal blood treatment modalities. Still further, in one or more embodiments, the accumulated heparin volume may be selected to be within the dependent set of the plurality of parameters in response to the configuration of the extracorporeal blood treatment apparatus.

In one or more embodiments, the discretionary set of the plurality of parameters may include one or more of transmembrane pressure, conductivity, plasma conductivity, total set ultrafiltration volume, and temperature.

In one or more embodiments, the treatment record may further include a signature block to receive a signature of a user, and the computing apparatus may be further configured to execute or the method may further include allowing a user to sign the signature block displayed on the graphical user interface.

In one or more embodiments, the treatment record may further include a treatment summary, and the treatment summary may include one or more of treatment date, treatment start time, treatment type, access type, and treatment duration.

In one or more embodiments, the treatment record may further include a notes region to receive notes from a user and the computing apparatus may be further configured to execute or the method may further include allowing a user to add alphanumeric text to the notes region of treatment record displayed on the graphical user interface.

In one or more embodiments, the computing apparatus may be further configured to execute or the method may further include allowing a user to enter disposable element information for each of the one or more disposable elements of the extracorporeal blood treatment apparatus, the disposable element information may include a disposable element lot number, and the treatment record may further include the disposable element information. Further, in one or more embodiments, the computing apparatus may further include a barcode scanner, and allowing a user to enter disposable element information may include scanning a barcode on the one or more disposable elements using the barcode scanner. In one or more embodiments, the display may include a touchscreen.

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

BRIEF DESCRIPTION OF THE DRAWING

FIG. 4 depicts an exemplary treatment record.

DETAILED DESCRIPTION OF EXEMPLARY EMBODIMENTS

Figure 1:
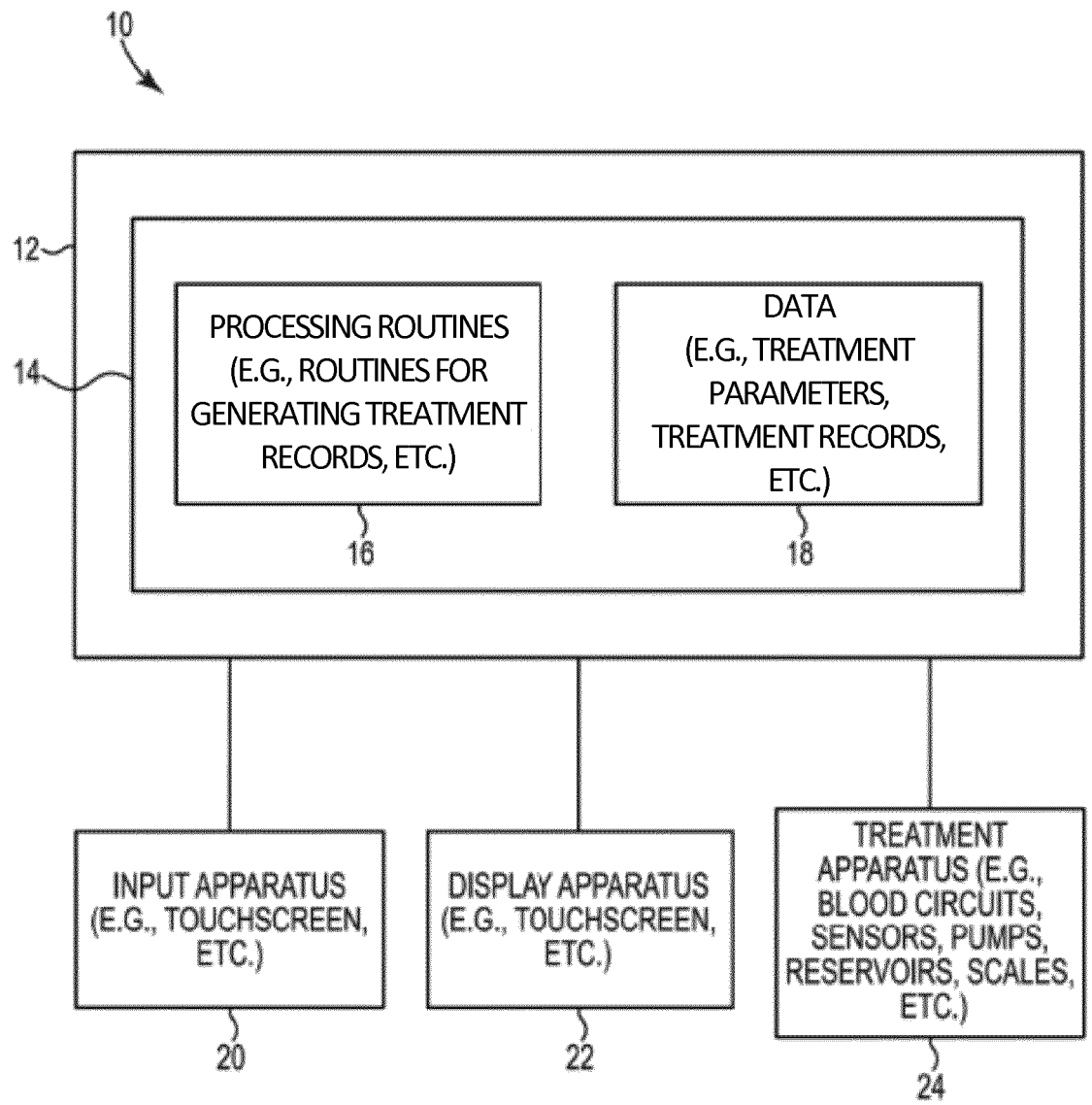
FIG. 1 is a block diagram of an exemplary medical treatment system including input apparatus, display apparatus, and treatment apparatus that may utilize the graphical user interfaces and methods described herein.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems, methods, and graphical user interfaces for use with medical treatment apparatus such as, e.g., extracorporeal blood treatment apparatus, shall be described with reference to FIGS. 1-8. It will be apparent to one skilled in the art that elements or processes from one embodiment may be used in combination with elements or processes of the other embodiments, and that the possible embodiments of such systems, methods, and graphical user interfaces using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

The exemplary systems and methods may provide for the generation of treatment records, e.g., using an exemplary graphical user interface (e.g., user-interactable graphical user interface, graphical user interface depicted on single-touch or multi-touch touchscreens, etc.). In particular, the exemplary graphical user interface may include one or more graphical regions, areas, and/or dialogs configured to allow for the selection of an extracorporeal blood treatment modality, selection of one or more discretionary treatment parameters to be included as part of, or within, a treatment record, display of a treatment record, ability to print a treatment record, ability to electronically transfer a treatment record, add notes to a treatment record, edit a treatment record, and/or ability to sign a treatment record as will be described further herein.

An exemplary extracorporeal blood treatment system 10 depicted in FIG. 1 may be used to execute, or perform, the methods and/or processes described herein. In at least one embodiment, the system 10 may be a machine for the extracorporeal treatment of blood. The system 10 could, for example, alternatively be a blood processing device or a blood component preparation device or other medical apparatus for fluid delivery/collection.

As shown, the exemplary extracorporeal blood treatment system 10 includes computing apparatus 12. The computing apparatus 12 may be configured to receive input from input apparatus 20 and transmit output to display apparatus 22. Further, the computing apparatus 12 may include data storage 14. Data storage 14 may allow for access to processing programs or routines 16 and one or more other types of data 18 (e.g., treatment parameters, patient information, treatment information, compulsory sets of parameters, dependent sets of parameters, discretionary sets of parameters, graphical regions, graphical elements, graphical areas, graphical settings cards, metrics, variables, images, values, limits, text strings, macros, etc.) that may be employed to perform, or carry out, exemplary methods and/or processes (e.g., generating treatment records, allowing adjustment of which parameters are recorded in treatment records, displaying graphical user interfaces, allowing user interaction with graphical user interfaces, interpreting touch gestures on a touchscreen (e.g., swipes, drags, press-and-hold, touches, presses, etc.), displaying graphical elements, displaying graphs, displaying textual elements, displaying textual values, displaying status information, issuing alarms, running a treatment, determining problems with a treatment, exchanging/changing reservoirs, notifying operators/users of problems, etc.) for use in performing extracorporeal blood treatments. The computing apparatus 12 may be operatively coupled to the input apparatus 20 and the display apparatus 22 to, e.g., transmit data to and from each of the input apparatus 20 and the display apparatus 22. For example, the computing apparatus 12 may be operatively coupled to each of the input apparatus 20 and the display apparatus 22 using, e.g., analog electrical connections, digital electrical connections, wireless connections, bus-based connections, etc. As described further herein, an operator, or user, may provide input to the input apparatus 20 to manipulate, or modify, one or more graphical elements, graphical regions, and graphical areas displayed on the display apparatus 22 to, e.g., initiate one or more actions and/or processes related to the extracorporeal blood treatment system, indicate one or more actions and/or statuses related to one or more processes of the extracorporeal blood treatment system, etc.

Further, various devices and apparatus may be operatively coupled to the computing apparatus 12 to be used with the computing apparatus 12 to perform one or more extracorporeal procedures/treatments as well as the functionality, methods, and/or logic described herein. As shown, the system 10 may include input apparatus 20, display apparatus 22, and treatment apparatus 24 operatively coupled to the computing apparatus 12 (e.g., such that the computing apparatus 12 may be configured to use information, or data, from the apparatus 20, 22, 24 and provide information, or data, to the apparatus 20, 22, 24). The input apparatus 20 may include any apparatus capable of providing input to the computing apparatus 12 to perform the functionality, methods, and/or logic described herein.

For example, the input apparatus 20 may include a touchscreen (e.g., capacitive touchscreen, a resistive touchscreen, a multi-touch touchscreen, etc.), a mouse, a keyboard, a trackball, etc. A touchscreen may be part of (e.g., overlay) the display apparatus 22 such that, e.g., a user may use the touchscreen to interact (e.g., by touch) with a graphical user interface displayed on the display apparatus 22. For example, the input apparatus 20 may allow a user to interact with a graphical user interface including an operation region containing, or depicting, graphical elements, graphical regions, and graphical areas associated with and representative of (or corresponding to) one or more features or processes of the extracorporeal blood treatment system when used in conjunction with the display apparatus 22 (e.g., displaying the graphical user interface). Further, more specifically, the input apparatus 20 may allow a user to interact with a graphical user interface including a treatment record graphical region when used in conjunction with the display apparatus 22 (e.g., displaying the graphical user interface).

The display apparatus 22 may include any apparatus capable of displaying information to a user, such as a graphical user interface, etc., to perform the functionality, methods, and/or logic described herein. For example, the display apparatus 22 may include a liquid crystal display, an organic light-emitting diode screen, a touchscreen, a cathode ray tube display, etc. As described further herein, the display apparatus 22 may be configured to display a graphical user interface that includes one or more graphical regions, graphical elements, and graphical areas (e.g., treatment record graphical regions, treatment selection graphical areas, etc.).

For example, the graphical user interface displayed by the display apparatus 22 may include, or display, an operation region that may include multiple graphical regions, graphical areas, and graphical elements related to the extracorporeal blood treatment system and/or for control of one or more processes during a treatment cycle (e.g., before treatment, during treatment, and after treatment). Such graphical regions, graphical areas, and graphical elements may include a treatment record graphical region configured to allow a user to view, edit, add notes to, print, and/or sign a treatment record of a treatment performed by the extracorporeal blood treatment system.

As used herein, a "region" of a graphical user interface may be defined as a portion of the graphical user interface within which information may be displayed or functionality may be performed and/or controlled by a user. Regions may exist within other regions, which may be displayed separately or simultaneously. For example, smaller regions may be located within larger regions, regions may be located side-by-side, etc. Additionally, as used herein, an "area" of a graphical user interface may be defined as a portion of the graphical user interface located within a region that is smaller than the region within which the area is located. Still further, as used herein, an "element" of a graphical user interface may be defined as a component of the graphical user interface that may be located within, or adjacent to, a region, an area, or another element. In one or more embodiments, an "element" of a graphical user interface may include a perimeter, or border, defining the outer edge, or boundary, of the element. In one or more embodiments, an "element" of a graphical user interface is a defined, finite portion, item, and/or section of a graphical user interface.

The processing programs or routines 16 may include programs or routines for performing treatment record generation, data recording, computational mathematics, touch-screen gesture interpretation algorithms, process performance algorithms, process automation algorithms, matrix mathematics, standardization algorithms, comparison algorithms, or any other processing required to implement one or more exemplary methods and/or processes described herein. Data 18 may include, for example, discretionary sets of parameters, compulsory sets of parameters, dependent sets of parameters, treatment records, patient parameters, machine parameters, patient information, treatment information, clinic information, printable treatment record documents, variables, graphics (e.g., graphical elements, graphical areas, graphical regions, treatment record graphical regions, icons, buttons, windows, dialogs, pull-down menus, 3D graphics, images, animations, etc.), graphical user interfaces, alarm data, fluid data, flow rates, fluid volumes, notifications, pressures, pressure limits, blood flow, blood flow limits, fluid removal rates, fluid removal limits, target blood temperatures, blood temperature limits, heuristics indicative of malfunction, results from one or more processing programs or routines employed according to the disclosure herein, or any other data that may be necessary for carrying out the one and/or more processes or methods described herein.

In one or more embodiments, the system 10 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The program used to implement the methods and/or processes described herein may be provided using any programmable language, or code, e.g., a high level procedural and/or object orientated programming language or code that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein. Further, in at least one embodiment, the system 10 may be described as being implemented by logic (e.g., object code) encoded in one or more non-transitory media that includes code for execution and, when executed by one or more processors, is operable to perform operations such as the methods, processes, and/or functionality described herein.

The computing apparatus 12 may be, for example, any fixed or mobile computer system (e.g., a controller, a microcontroller, a personal computer, mini computer, etc.). The exact configuration of the computing apparatus 12 is not limiting, and essentially any device capable of providing suitable computing capabilities and control capabilities (e.g., graphics processing, control of extracorporeal blood treatment apparatus, etc.) may be used.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 12 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

The methods and/or logic described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

The treatment apparatus 24 may include any apparatus used by an exemplary extracorporeal blood treatment system capable of performing extracorporeal blood treatments, such as, e.g., blood circuits, sensors, pumps, reservoirs, scales, treatment sets, filters, pressure sensors, etc. For example, the treatment apparatus 24 may include one or more elements, or components, of the extracorporeal blood treatment system 100 described herein with reference to FIG. 2.

The exemplary systems, and exemplary methods performed, or used, by such exemplary systems, described herein may include systems such as, e.g., dialysis systems. The general term "dialysis" as used herein includes hemodialysis, hemofiltration, hemodiafiltration, hemoperfusion, liver dialysis, and therapeutic plasma exchange (TPE), among other similar treatment procedures. In dialysis generally, blood is taken out of the body via an arterial blood circuit and exposed to a treatment device to separate substances therefrom and/or to add substances thereto, and is then returned to the body via a venous blood circuit. Although extracorporeal blood treatment systems capable of performing general dialysis (as defined above, including TPE) shall be described herein with reference to the exemplary extracorporeal blood treatment system of FIG. 2, other systems such as those for infusion of drugs, performance of continuous renal replacement therapy (CRRT), extracorporeal membrane oxygenation (ECMO), hemoperfusion, liver dialysis, apheresis, TPE, etc. may benefit from the systems, methods, and apparatus described herein and the present disclosure is not limited to any particular treatment system.

Figure 2:
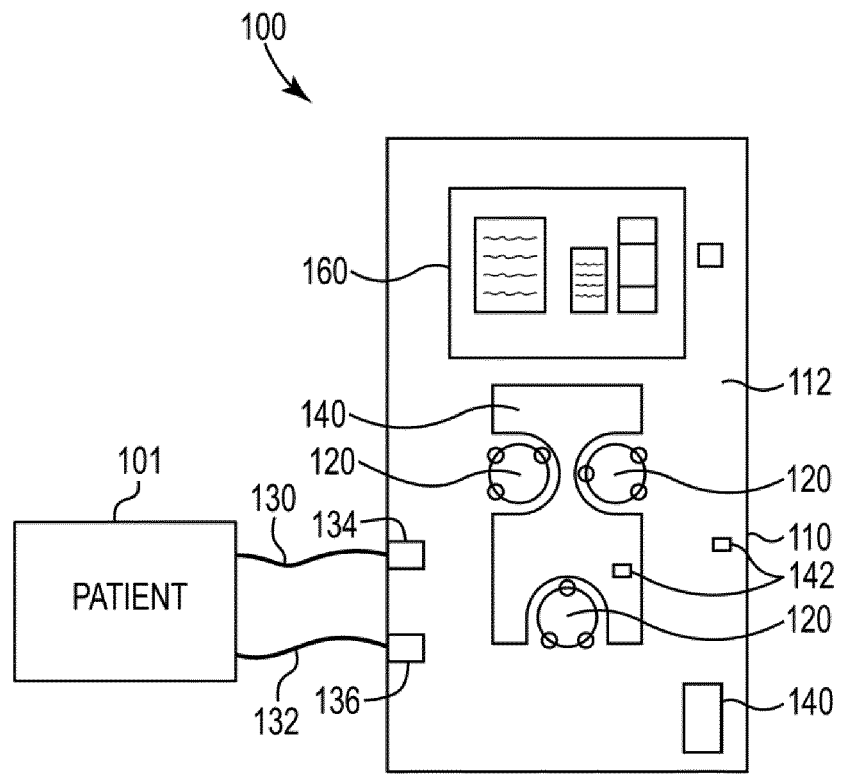
FIG. 2 is an illustration of an exemplary extracorporeal blood treatment system that may include graphical user interfaces and may utilize the methods described herein.

Referring to FIG. 2, one illustrative embodiment of an extracorporeal blood treatment system, or apparatus, 100 is depicted. The system 100 includes a housing 110 having a front face 112. The system 100 further includes one or more pumps 120, one or more disposable elements 140 (e.g., including or part of integrated modules), and one or more sensors 142 for use in performing one or more extracorporeal blood treatments. The one or more pumps 120 may be used to move liquids through the system as part of a treatment process. Although the pumps 120 are depicted in the form of peristaltic pumps, the pumps used in the extracorporeal blood treatment system described herein may be provided in a variety of alternative forms, e.g., piston pumps, pumps for use with syringes, diaphragm pumps, etc. and/or may not be visible on the outside of the housing 110. The one or more disposable elements 140 may be coupled to the system 100 for using in performing the extracorporeal blood treatment. The one or more disposable elements 140 may include one or more fluid circuits such as, e.g., dialysis or dialysate fluid circuits, blood circuits, etc. and/or one or more blood treatment units such as, e.g., filters, etc. In at least one embodiment, a disposable element 140 is a cartridge or integrated unit including a plurality of various parts or portions configured to perform the extracorporeal blood treatment. Additionally, the one or more disposable elements 140 may include containers, or vessels, containing, or holding, one or more substances for use in the performance of the extracorporeal blood treatment. For example, a disposable element 140 may include a container, or vessel, holding bicarbonate, citrate, and/or dialysate/dialysis fluid, which may be operatively coupled to the dialysis/dialysate fluid circuit. Further, the disposable elements 140 may be described as providing at least a portion of the extracorporeal blood treatment fluid circuit that may be operatively coupled to one or more pumps 120 and one or more sensors 142 of the system 100 for use in performing extracorporeal blood treatments. As shown, two disposable elements 140 appear to be coupled to the front face 112 of the housing 110 of the system 100 to, e.g., integrate with the one or more other fluid circuits, pumps 120, and sensors 142 of the system 100.

As described herein, the one or more disposable elements 140 may be described as including one or more disposable fluid circuits and one or more blood treatment units operatively coupled to the one or more disposable fluid circuits. The one or more disposable elements 140 may be further described as including a blood circuit for receiving, circulating, and returning blood from/to a patient. The blood circuit may include one or more blood lines (e.g., as part of a disposable element). Further, the one or more disposable elements 140 may be further described as including a dialysis/dialysate circuit operatively coupled, or couplable, to the blood circuit to remove waste from the blood of the patient. The dialysis/dialysate circuit may receive, circulate, and return dialysis/dialysate fluid (e.g., returning dialysis/dialysate fluid including waste). The dialysis/dialysate circuit may include one or more dialysis/dialysate lines (e.g., as part of a disposable element 140). The blood treatment units may be, for example, a plasma filter, a hemodialysis filter, a hemofiltration filter, etc. Generally, the blood treatment units may be referred to as "filters."

As described herein, the system 100 may further include one or more sensors 142. As shown, two sensors 142 are identified on the system 100. One sensor 142 is located on, or coupled to, the front surface 112 of the housing 110 and another sensor 142 is located on the, or coupled to, the disposable elements 140. Additionally, the system 100 may include sensors 142 that are not visible on the outside of the housing 110, and instead, may be internal to the system 100 (e.g., within the housing 110). Generally, the system 100 may include any one or more sensors 142 so as to be able to monitor any value (e.g., any aspect, setting, level, condition, event internal to the system 100, etc.) of any process feature of the system 100 such as, e.g., process features during the performance of one or more extracorporeal blood treatments. For example, the system 100 may include one or more pressure sensors 142 operable to measure, or monitor, various pressures of various circuits, chambers, pods, reservoirs, etc. of the system 100, e.g., during the performance of an extracorporeal blood treatment, during the performance of a pre-treatment process, during the performance of a disinfection, post-treatment process, etc. Further, for example, the system 100 may include one or more flow rate sensors 142 operable to measure, or monitor, various fluid flow rates of fluids within various circuits, chambers, pods, reservoirs, etc. of the system 100, e.g., during the performance of an extracorporeal blood treatment, during the performance of a pre-treatment process, during the performance of a disinfection, post-treatment process, etc. Specifically, the system 100 may include one or more blood-related parameter sensors 142 such as, e.g., flow rate sensors to monitor various blood flow rates throughout the blood circuits of the system 100, blood pressure sensors to monitor the diastolic and systolic blood pressure of the patient, blood circuit pressure sensors to monitor the arterial and venous blood lines pressures, heart rate sensors to measure the patient's heart rate, etc. Further, for example, the system 100 may include one or more waste sensors 142 configured to, or operable, to measure, or monitor, an amount of waste being removing from a patient (e.g., from a patient's blood), e.g., during the performance of an extracorporeal blood treatment. Further, for example the system 100 may include one or more fluid circuit or lines sensors 142 such as, e.g., blood circuit sensors to detect whether a blood circuit is coupled or uncoupled to the system, dialysate/dialysis fluid circuit sensors to detect whether a dialysate/dialysis circuit is coupled or uncoupled to the system, etc. In other words, one or more blood circuit sensors may be configured to detect whether a blood circuit is operatively coupled to the remainder of the extracorporeal blood treatment apparatus for use in an extracorporeal blood treatment and/or one or more dialysate/dialysis fluid circuit sensors may be configured to detect whether a dialysate/dialysis circuit is operatively coupled to the remainder of the extracorporeal blood treatment apparatus for use in an extracorporeal blood treatment. In one or more embodiments, the blood circuit and dialysate/dialysis fluid circuits may include some or all of the same sensors (e.g., when the blood circuit and dialysate/dialysis fluid circuit are part of the same disposable element or cartridge). Still further, for example, the system 100 may include other sensors 142 such as fluid level sensors, temperature sensors, leak detection sensors, etc. that may be used before an extracorporeal blood treatment is performed, during the performance of an extracorporeal blood treatment, and/or after an extracorporeal blood treatment is performed.

Additionally, the extracorporeal blood treatment fluid circuit of the system 100 may be described as being completed by a combination of the disposable elements 140 and the system 100 and may be generally described as defining a blood circuit that removes blood from a patient, for example, via a catheter inserted in a vascular access of the patient, and takes the blood though a blood removal line. Then, the blood may pass through a chamber (e.g., a blood chamber) and, via a return line, may be transported back to the patient.

In one or more embodiments, the extracorporeal blood treatment system 100 may be configured for acute blood treatments (e.g., continuous renal replacement therapy) and may also include one or more devices, apparatus, and structures configured to perform the acute blood treatments. For example, the extracorporeal blood treatment system 100 may include reservoir sensors, or scales, (e.g., weight sensors, load cells, etc.), each of which is configured to hold and weigh a reservoir. The reservoir sensors may be positioned below the bottom end of the housing 110, at least in part because the reservoirs are typically attached to and hang from the reservoir sensors. The extracorporeal blood treatment systems described herein may include one or more reservoir sensors and associated reservoirs such as, e.g., as few as two reservoirs sensors and associated reservoirs, four or more reservoirs sensors and associated reservoirs, etc.

The extracorporeal blood treatment system 100 further includes a venous blood line/circuit 130 extending from a patient 101 (symbolically represented in FIG. 2) to the housing 110 to return blood to the patient 101 after the blood is treated by the system 100, an arterial blood line/circuit 132 extending from the patient 101 to the housing 110 to withdraw blood from the patient 101 for treatment, a venous blood circuit pressure sensor 134 configured to measure, or monitor, the pressure of the venous blood line/circuit 130 (e.g., the pressure of the blood, or fluid, within the venous blood line/circuit 130), and an arterial blood circuit pressure sensor 136 configured to measure, or monitor, the pressure of the arterial blood line/circuit 132 (e.g., the pressure of the blood, or fluid, within the arterial blood line/circuit 132). The venous and arterial blood circuits 130, 132 may connect the patient to a blood circuit (e.g., a disposable element 140) such that, e.g., blood of the patient may be circulated through the blood circuit to perform blood treatments thereon. In other words, the blood circuit may be connectable to a patient using the venous and arterial blood lines 130, 132.

The extracorporeal blood treatment system 100 also includes a display 160 used to show, or convey, information to an operator or user. The display 160 may also serve as an input device if, e.g., the display 160 is in the form of a touchscreen (e.g., a user interactable graphical user interface, a touchscreen keyboard, etc.). Also, although the display 160 is depicted as being located in the housing 110, in one or more alternate embodiments, the display 160 may be separate from the housing 110 of the extracorporeal blood treatment system 100. For example, the display 160 may be movably (e.g., swivel, tilt, etc.) attached, or coupled, to the housing 110 (e.g., a top end of the housing 110).

As shown in FIG. 1 and as related to FIG. 2, the treatment apparatus 24 may be operatively coupled, or connected, to the computing apparatus 12. Among the treatment apparatus 24 operably coupled to the computing apparatus 12 may be the pumps 120, blood circuits/lines 130, 132, blood circuit pressure sensors 134, 136, and disposable elements 140 as shown in FIG. 2.

Exemplary graphical user interfaces, or portions thereof, for use in displaying information related to extracorporeal blood treatments, displaying and manipulating treatment records, providing functionality for the generation of treatment records, providing functionality to a user for use in preparing and performing extracorporeal blood treatments (e.g., controlling performance and/or one or more processes of a treatment), and/or configuring or maintaining an extracorporeal blood treatment system are depicted in FIGS. 5-8. Such exemplary graphical user interfaces may be depicted by the display apparatus 22 of the system 10 described herein with reference to FIG. 1 and/or the display 160 of the system 100 of FIG. 2. Additionally, the graphical user interfaces described herein may be depicted on a touchscreen, and in such configuration, the input apparatus would also be the touchscreen.

Each exemplary graphical user interface of the exemplary extracorporeal blood treatment systems and methods described herein may include one or more graphical elements, regions, and areas used to display information to a user. A user may use input apparatus 20 of the exemplary extracorporeal blood treatment system 10 described herein with reference to FIG. 1 to select or manipulate graphical elements, regions, and areas of the exemplary graphical user interfaces of FIGS. 5-8. As used herein, when a user "selects" or "interacts with" a graphical element, area, and/or region of the graphical user interface, it is to be understood that "selecting" or "interacting with" the graphical element, area, and/or region to perform one or more tasks or steps may be conducted in many different ways using many different types of input apparatus. For example, when the input apparatus includes a touch screen, a user may select or interact with a graphical element, area, and/or region by "touching" the graphical region with their finger or using a pointing device such as a stylus. Further, for example, when the input apparatus includes a mouse or similar pointing device, a user may select or interact with a graphical element, area, and/or region by locating an arrow or cursor over the desired graphical region "clicking" the graphical region. Still further, for example, when the input apparatus includes a series of buttons and/or knobs, a user or user may select or interact with a graphical element, area, and/or region by using the buttons and/or knobs to navigate to the graphical region and to select it (e.g., by depressing the button and/or knob). Additionally, it is to be understood that selection of or interaction with a graphical element, area, and/or region may be conducted using various gestures such as, for example, but not limited to, swipes, double taps, select-and-drag, press, tracing of various shapes, pinch-inwardly, pinch-outwardly, finger spread, multi-finger touches and/or swipes, etc.

Figure 3:
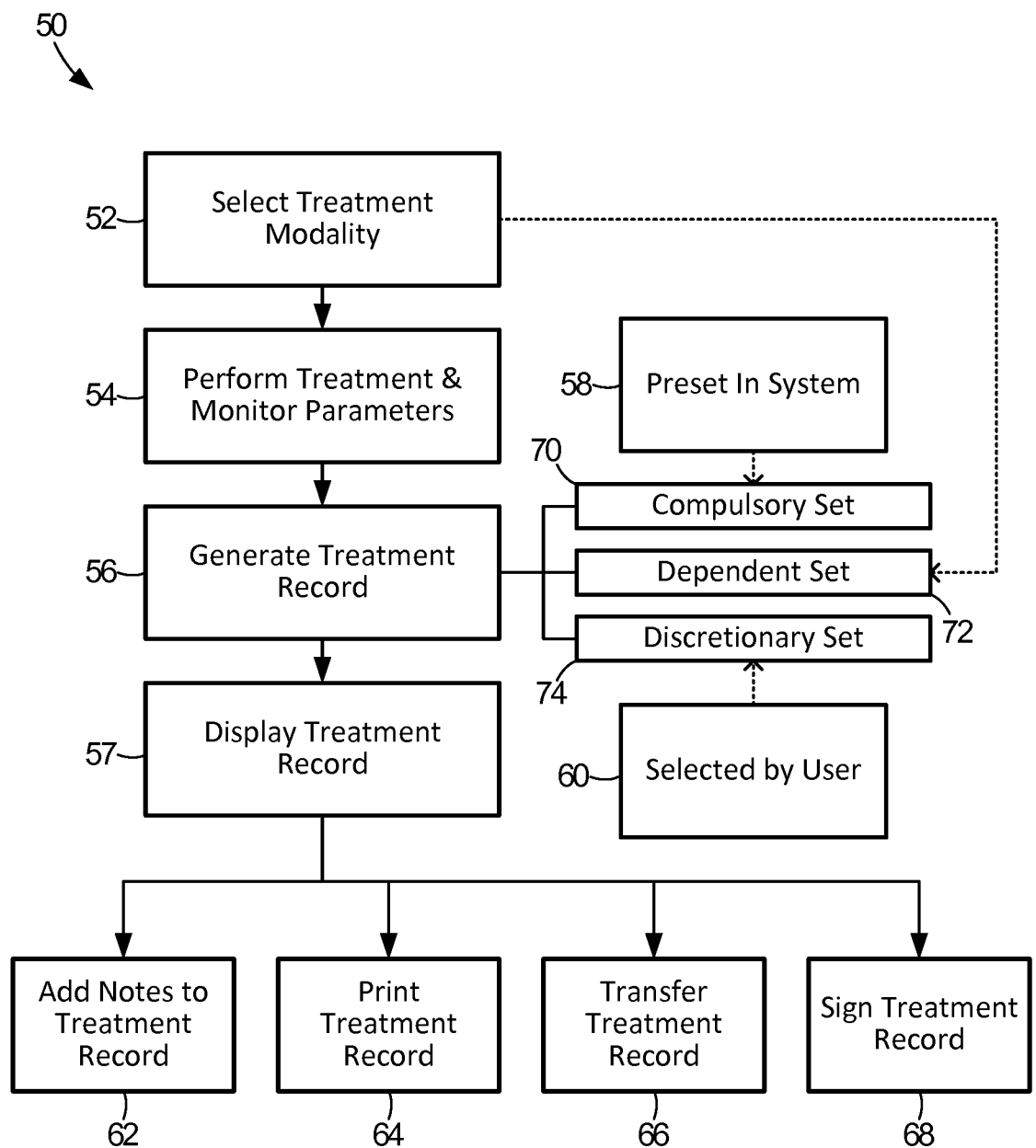
FIG. 3 is a block diagram of exemplary methods and processes for use in providing treatment records with an exemplary graphical user interface of extracorporeal blood treatment systems such as, for example, shown generally in FIGS. 1-2.

An exemplary method 50 for use in providing, or generating, a treatment record for an extracorporeal blood treatment is depicted in FIG. 3. The method 50 may include the selection of a treatment modality 52 from a plurality of different treatment modalities. For example, the plurality of treatment modalities may include hemodialysis, hemodiafiltration predilution, hemodiafiltration postdilution, hemofiltration, hemoperfusion, liver dialysis, and therapeutic plasma exchange (TPE). An exemplary graphical user interface 200 depicting the selection of a treatment modality is shown in FIG. 5.

Figure 5:
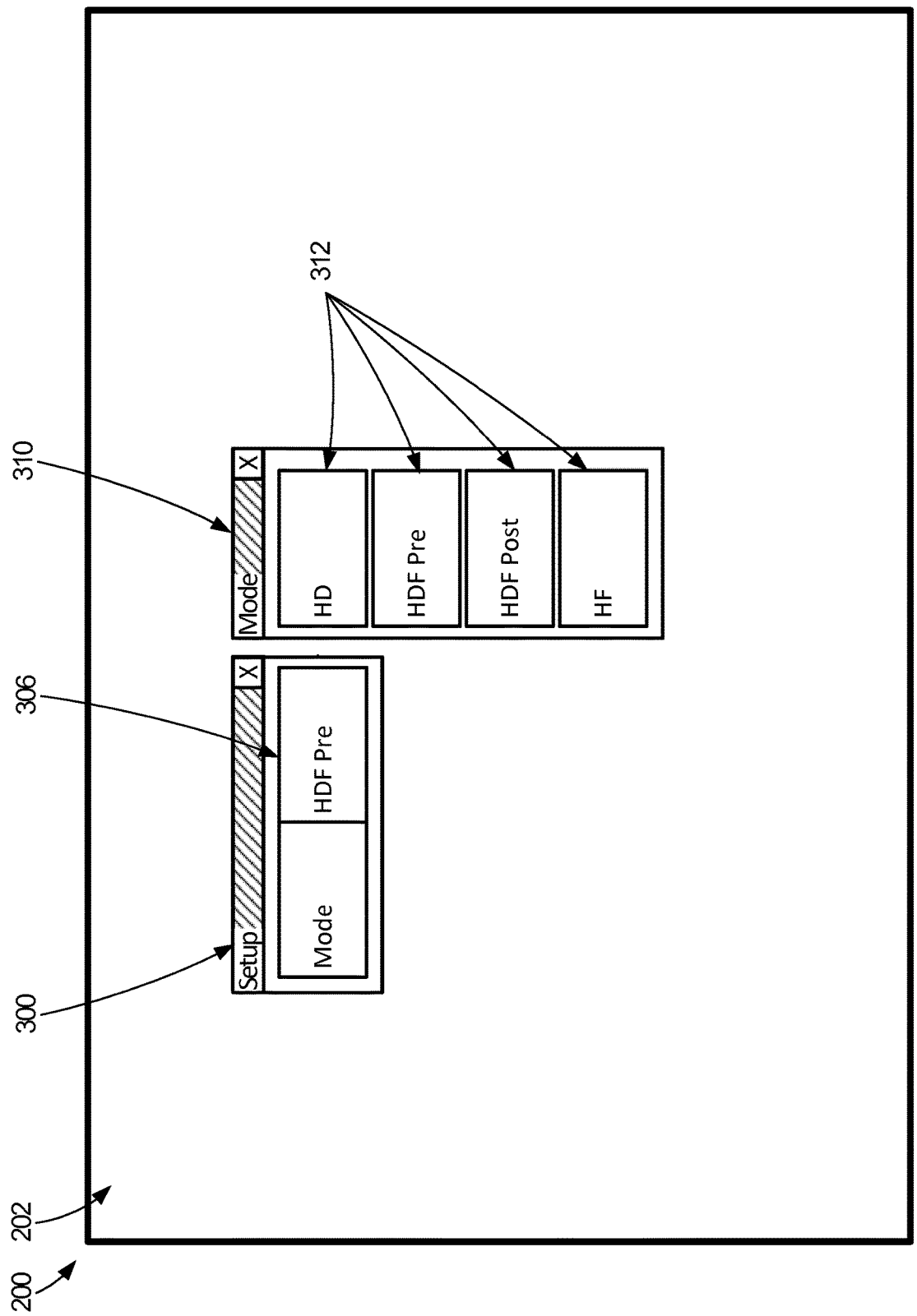
FIG. 5 depicts an exemplary graphical user interface displaying a treatment selection graphical area for use with extracorporeal blood treatment systems such as, for example, shown generally in FIGS. 1-2.

The graphical user interface 200 of FIG. 5 includes an operation region 202. Within the operation region 202, a setup graphical area 300 is displayed. The setup graphical area 300 may be labelled "Setup" and include a treatment modality graphical area 306. The treatment modality graphical area 306 depicts the word "Mode" and the presently-selected treatment modality, "HDF Pre," hemodiafiltration predilution. If a user would like to change the presently-selected treatment modality, e.g., from HDF Pre to another treatment modality, the user may select (e.g., touch, click, etc.) an area of the treatment modality graphical area 306 such as, e.g., the presently-selected treatment modality, to display, or depict, a treatment modality selection graphical area 310.

The treatment modality selection graphical area 310 may include a plurality of treatment modalities 312. As shown, the plurality of treatment modalities 312 include "HD, i.e., hemodialysis, "HDF Pre," i.e., hemodiafiltration predilution, "HDF Post," i.e., hemodiafiltration postdilution, and "HF," i.e., hemofiltration. A user may select (e.g., touch, click, etc.) one of the plurality of treatment modalities 312 of the treatment modality selection graphical area 310 to change the presently-selected treatment modality. For example, if a user would like to change the presently-selected treatment modality from hemodiafiltration predilution to hemodialysis, then the user may select the "HD" treatment modality 312 of the treatment modality selection graphical area 310, which in turn, would change the treatment modality displayed within the treatment modality graphical area 306.

Figure 6:
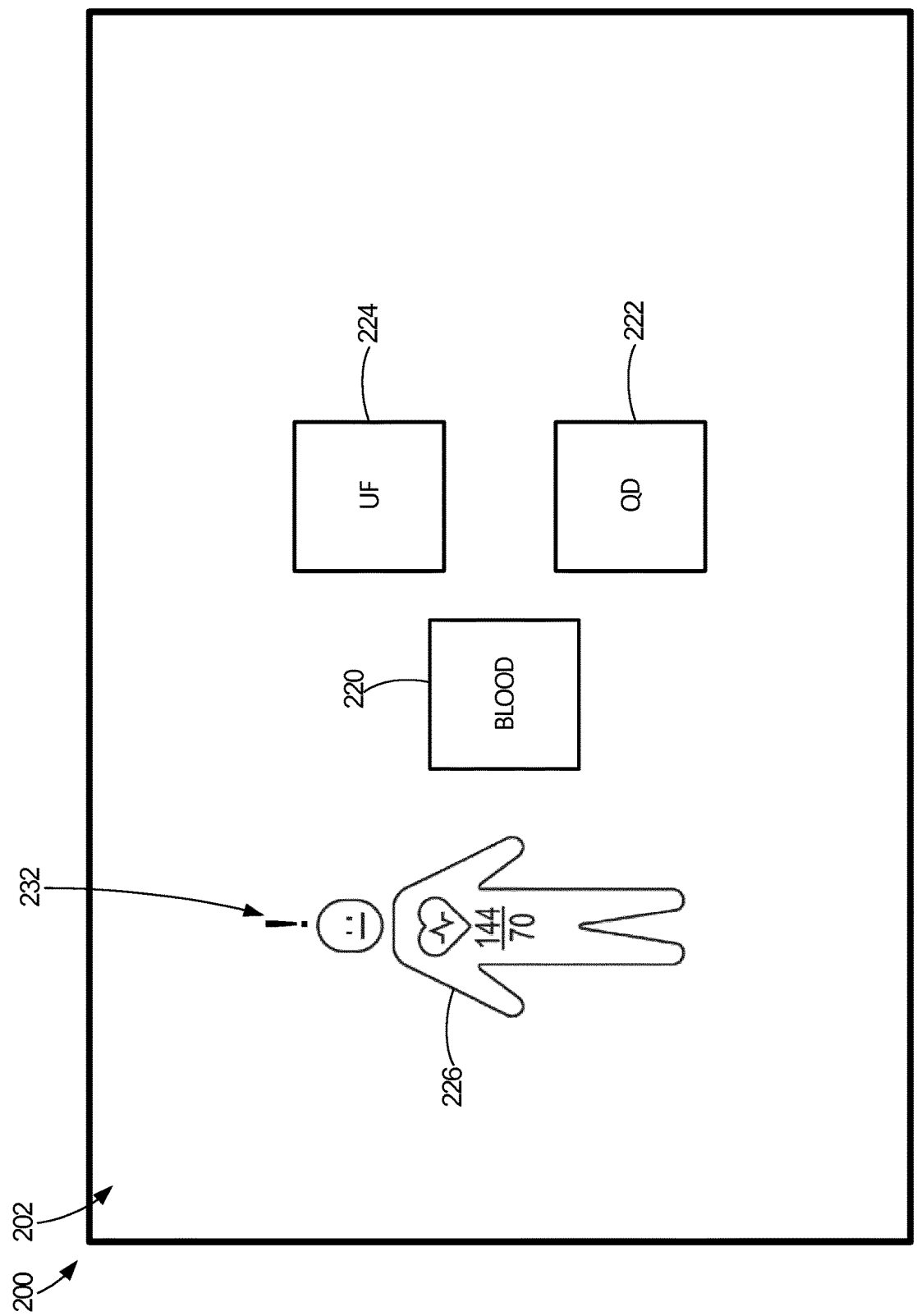
FIG. 6 depicts the graphical user interface of FIG. 5 displaying a plurality of graphical elements for use in the performance of an extracorporeal blood treatment.

After selection of the treatment modality 52, e.g., using the graphical user interface 200 of FIG. 5, the exemplary method 50 may perform an extracorporeal blood treatment 54 according to the selected treatment modality. During the treatment, the exemplary blood treatment system may monitor a plurality of parameters 54 using extracorporeal blood treatment apparatus from the treatment system itself and also the patient. Further, during the blood treatment 54, the operation region 202 of the graphical user interface 200 as shown in FIG. 6 may display a plurality of graphical elements used to perform various processes and display various information with respect to the treatment. More specifically, the operation region 202 may include a blood graphical element 220 configured to perform various processes and display information related to the patient's blood, a dialysate ("QD") graphical element 222 configured to perform various processes and display information related to dialysate, and an ultrafiltration graphical element 224 ("UF") configured to perform various processes and display information related to ultrafiltration.

The operation region 202 further includes a human-shaped graphical element 226 configured to perform various processes and display information related to the patient. For example, the human-shaped graphical element 226 may be selected to perform a pulse measurement or blood pressure measurement or may be moved (e.g., selected and dragged) to indicate whether a patient is connected or disconnected from a blood/dialysate circuit of the blood treatment system. Further, as shown, the human-shaped graphical element 226 may further display the patient's systolic and diastolic blood pressure.

When a blood treatment has ended such as, for example, at the end of the treatment, a treatment record may be generated 56. The treatment record may include various information related to the patient, the extracorporeal blood treatment system, and/or the blood treatment that was performed. For example, an exemplary treatment record 40 is depicted in FIG. 4, which may be printed onto one or more sheets of paper and/or may be generated as an electronic document. As shown, the treatment record 40 may include patient and treatment information 41 and a plurality of values over time for a plurality of parameters 43 measured, or monitored, by the extracorporeal blood treatment apparatus during the treatment.

The patient and treatment information 41 may include one or more of patient name, patient identifier, treatment date, treatment start time, system identifier, clinic name, and treatment modality. As shown in FIG. 4, the patient and treatment information 41 includes a patient name, i.e., "Jack Johanssen," a treatment start time, i.e., "13:36," a clinic name, "ABC Clinic," and an extracorporeal blood treatment machine name, i.e., "XYZ Machine."

As shown in the treatment record 40 of FIG. 4, the plurality of values over time for a plurality of parameters 43 may be numerically depicted in a cascading list, or column, over time. Each column includes a different parameter as identified at the top of the column. The plurality of values for each parameter may be sampled, or recorded, in the treatment record 40 periodically throughout the treatment. The period of time between parameter value samplings may be referred to as a sampling time period, which may be between about 1 minute and about 2 hours. In at least one embodiment, the sampling time period may be about 15 minutes. The sampling time period may be greater than or equal to about 1 minute, greater than or equal to about 2 minutes, greater than or equal to about 5 minutes, greater than or equal to about 10 minutes, greater than or equal to about 15 minutes, greater than or equal to about 20 minutes, greater than or equal to about 45 minutes, greater than or equal to about 1 hour, etc. Further, the sampling time period may be less than or equal to about 1.5 hours, less than or equal to about 55 minutes, less than or equal to about 35 minutes, less than or equal to about 30 minutes, less than or equal to about 25 minutes, less than or equal to about 12 minutes, less than or equal to about 7 minutes, less than or equal to about 3 minutes, etc.

The time at which each parameter was recorded may be indicated in the leftmost column on the treatment record 40. The sampling time period may elapse between each of the times listed in the leftmost column. For example, as shown in FIG. 4, the sampling time period is 30 minutes, which is the period of time that elapses between two adjacent times noted in the leftmost column. Additionally, as shown in FIG. 4, an initial set of values may be recorded, or saved, into the treatment record 5 minutes after the start of the treatment and 5 minutes before the end of the treatment. In at least one embodiment, the sampling time period may be referred to as a "sampling rate." Further, in at least one embodiment, the first parameter values recorded into the treatment record 40 may be monitored, or sampled, five minutes after the start of the treatment, and the last, parameter values recorded into the treatment record 40 may be monitored, or sampled, five minutes before the end of the treatment.

Further, the values of the parameters may be monitored, or sampled, at times other than periodically according to the sampling time period such as in response to an event, or action, occurring in the system or with respect to a treatment. For example, the parameter values may be recorded into the treatment record 40 when a blood pressure measurement is performed and/or at the end of a treatment. Still further, parameter values may be monitored, or measured, before and after a treatment, and the parameter values recorded in the treatment record 40 before and after treatment may be indicated as being before or after treatment within the treatment record.

Further, the treatment record 40 may include a notes portion 44 for notes that a user may desire to add to the record, a treatment summary 45 for a summarization of the treatment performed, and a signature portion 46 for the signature of a user to, e.g., confirm or verify the information on, or contained within, the treatment record 40. As shown, the notes portion 44 includes the following note: "Patient hypertension after 2:30, gave saline bolus." The treatment summary 45 may include one or more of treatment date, treatment start, treatment type, access type, treatment time or duration, isolated ultrafiltration duration (e.g., if isolated ultrafiltration performed) dialysis dose (Kt/V), mean QB, mean systolic/diastolic pressure, mean pulse, ultrafiltration volume, isolated UF volume (e.g., if isolated ultrafiltration performed), relative blood volume, heparin type, and convective volume. As shown in FIG. 4, the treatment summary 45 is located in, or within, two areas on the treatment record 40 and includes treatment date, i.e., 2016 Jul. 30, treatment start time, i.e., 13:36, treatment type, i.e., "HD," an access type, i.e., double needle (DN), a treatment time or duration, 4:00, an ultrafiltration volume, i.e., 4.0, and a heparin type, i.e., Bolus.

The treatment record 40 generated may not include values for all of the monitored parameters. Instead, the treatment record 40 may include a subset of the monitored parameters, which, e.g., may be the most relevant for recordation purposes, etc. The subset of monitored parameters may be grouped into a plurality of sets or groups. For example, the treatment record may be generated 56 using a compulsory set of the plurality of parameters 70, a dependent set of the plurality of parameters 72, and a discretionary set of the plurality of parameters 74.

The compulsory set of the plurality of parameters 70 may not be set, or selected, by a user. Instead, the compulsory set of the plurality of parameters 70 may be preset in the system 58, and may not be changed by a user. In other words, the compulsory set of the plurality of parameters 70 may always be used in the generation of the treatment record 40 such that the values for the compulsory set of the plurality of parameters 70 are always included on the treatment record. The compulsory set of the plurality of parameters 70 may include one or more of blood flow rate, accumulated blood flow rate, venous pressure, arterial pressure, accumulated ultrafiltration volume, ultrafiltration rate, dialysate flow rate, dialysate sodium concentration, dialysate bicarbonate concentration (HC03), etc.

In one or more embodiments, an administrator for a clinic may modify the compulsory set of the plurality of parameters 70 that are preset for a blood treatment system or a plurality of blood treatment systems at the clinic. Further, in one or more embodiments, the compulsory set of the plurality of parameters 70 may be preset by a manufacturer and may not be able to be changed by a clinic administrator.

Some parameters may not be available and/or useful for recordation purposes for various treatment modalities and/or treatment configurations. Thus, a dependent set of the plurality of parameters 72 may be selected in response to at least the selection of the extracorporeal blood treatment modality and/or the configuration of blood treatment system. In other words, some of the plurality of parameters to be included on, or within, the treatment record 40 may be dictated by, or based on, the selection of a blood treatment modality and/or the configuration of the blood treatment system. The dependent set of the plurality of parameters 72 may include one or more of systolic blood pressure, diastolic blood pressure, pressure pulse, accumulated heparin volume, dialyzer clearance of urea, dialyzer clearance of urea multiplied by time divided by volume of distribution of urea (KT/V), dialyzer clearance of urea multiplied by time (KT), relative blood volume percentage, convective volume, convective clearance rate, etc. As shown in FIG. 4, the systolic blood pressure, diastolic blood pressure, and blood pressure pulse may be measured and recorded less often than many of the plurality of parameters 43. For example, often the systolic blood pressure, diastolic blood pressure, and blood pressure pulse measurements may be initiated by a user (e.g., selecting one or more graphical regions of the graphical user interface), and thus, may not be recorded at the same time as the periodically monitored and recorded parameters 43 (as shown, such systolic blood pressure, diastolic blood pressure, and blood pressure pulse values are measured and recording between periodic recordings such as between 3:30 and 3:00 at 2:55). Additionally, the systolic blood pressure, diastolic blood pressure, and pressure pulse values may be measured and recorded into the treatment record 40 before treatment (e.g., pre-treatment) and after treatment (e.g., post treatment). In other words, the systolic blood pressure, diastolic blood pressure, and blood pressure pulse values may be recorded in the treatment record 40 if taken by a user.

For example, if hemofiltration or hemodiafiltration is selected as the treatment modality or mode, then the dependent parameters convective volume and convective clearance rate may be selected to be within the dependent set of the plurality of parameters 72. Conversely, the selection of treatment modalities other than hemofiltration and hemodiafiltration may not initiate, or trigger, the selection of the dependent parameters convective volume and convective clearance rate to be within the dependent set of the plurality of parameters 72.

Additionally, the dependent set of the plurality of parameters 72 may be selected in response to the configuration of the blood treatment and/or system. For example, various treatment modalities may utilize heparin for anticoagulation. Thus, when a treatment uses heparin, accumulated heparin volume may be selected to be within the dependent set of the plurality of parameters 72. Conversely, when heparin is not used within a blood treatment, accumulated heparin volume may not be selected to be within the dependent set of the plurality of parameters 72.

Some of the plurality of parameters may be described as being discretionary because, e.g., such parameters may be selected by a user at the user's discretion. For example, a user may use the graphical user interface 200 to select one or more of a plurality discretionary parameters 60 to be included within a discretionary set of the plurality of parameters 74. The discretionary set of the plurality of parameters 74 may include one or more of transmembrane pressure, conductivity, plasma conductivity total set ultrafiltration volume, temperature, etc.

The compulsory set of parameters 70, the dependent set of parameters 72, and the discretionary set of parameters 74 may form, or define, the superset of parameters 43 that are recorded on the treatment record 40. Further, in one or more embodiments, each of the compulsory set 70, the dependent set 72, and the discretionary set 74 may be separated or delineated from one another on the treatment record 40 such that, e.g., a user may be able to recognize each set 70, 72, 74 from each other. In other embodiments, all of the sets 70, 72, 74 may grouped together so as to be indistinguishable from each other on the treatment record 40.

Figure 7:
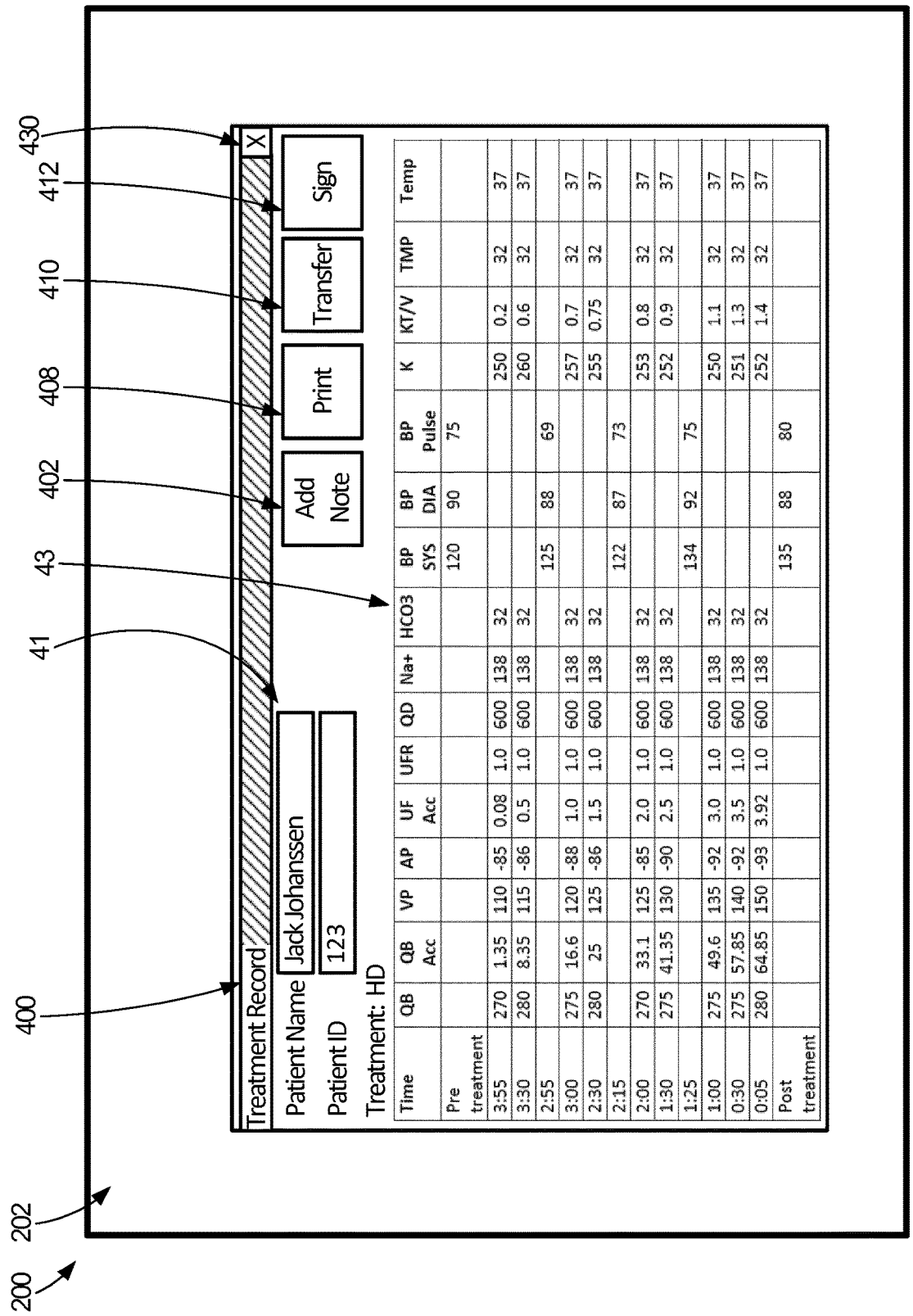
FIG. 7 depicts the graphical user interface of FIGS. 5-6 displaying a treatment record.

The method 50 may further include displaying 57 the treatment record 400 electronically on the graphical user interface 200 as shown in FIG. 7. The display 57 of the treatment record 400 may be triggered, or initiated, in multiple ways. For example, the treatment record 400 may be displayed in response to the end of a blood treatment. For instance, a blood treatment may be completed, and upon completion of the blood treatment, the treatment record 400 may be automatically displayed on the graphical user interface 200, e.g., over a majority of the remainder of the operation region 202. Further, for instance, a patient may be prematurely disconnected from the blood treatment system ending the blood treatment early before completion, and upon disconnection from the blood treatment system, the treatment record 400 may be automatically displayed on the graphical user interface 200.

Further, the treatment record 400 may be displayed on the graphical user interface 200 in response to user interaction. For example, a user may select a graphical region, graphical area, and/or graphical element of the graphical user interface 200 to trigger, or initiate, the display of the treatment record 400 during or after the completion of a treatment. For example, a user may select a portion of the human-shaped graphical element 226 of FIG. 6 to display the treatment record 400.

Further, for example, the exemplary systems and methods may provide a notification to a user to indicate to the user that a treatment record may, or should, be displayed. For instance, a treatment record indication 232, which in the embodiment of FIG. 6 is a flashing, or blinking, exclamation point ("!"), may be displayed in the operations region 202, e.g., proximate the human-shaped graphical element 226.

Upon selection of the treatment record indication 232, the treatment record 400 of FIG. 7 may be displayed.

The treatment record 400 may include the same, or similar, information as shown on the treatment record 40 of FIG. 4. For example, the treatment record 400 may include patient and treatment information 41 and a plurality of values of parameters 43 as shown in FIG. 7. Additionally, although not shown in FIG. 7, the treatment record 400 may include all of the information and graphical regions, areas, and elements of the treatment record 40 of FIG. 4.

Once the treatment record 400 is displayed on the graphical user interface 200, a user may perform various actions with respect to the treatment record 400. For example, the method 50 may further include allowing a user to add notes to the treatment record 62 as described further herein with respect to FIG. 8, to print the treatment record 64, to transfer the treatment record 66, and to sign the treatment record 68 using the graphical user interface 200.

Figure 8:
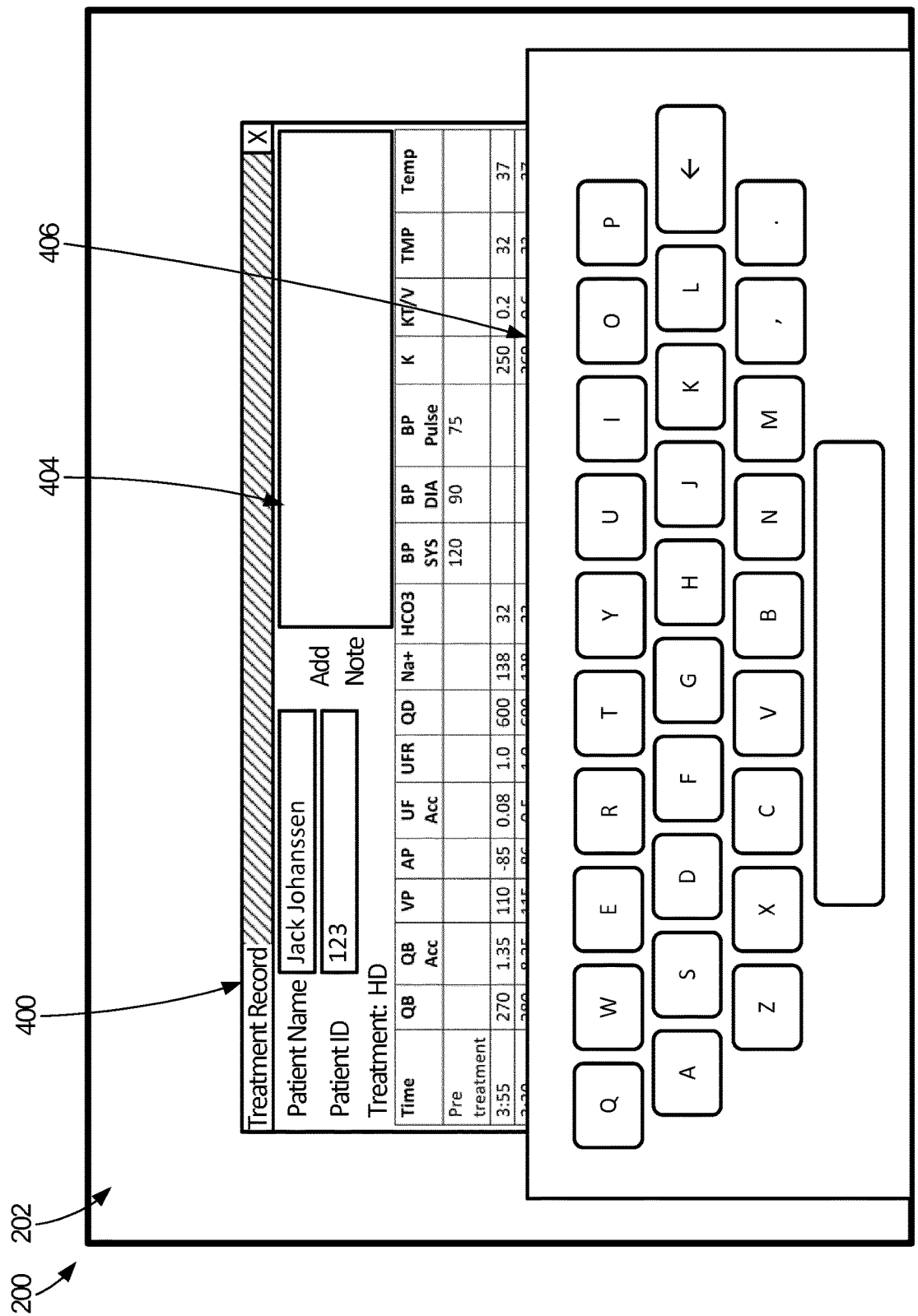
FIG. 8 depicts the graphical user interface of FIG. 7 including a keyboard graphical area for inputting notes into the treatment record.

For example, the treatment record 400 may include an add note graphical element 402, which, upon selection, may display a notes region 404 as shown in FIG. 8. The notes region 404 may be configured to receive notes from a user using an on-screen keyboard 406. More specifically, a user may add alphanumeric text to the notes region 404 of treatment record 400 using the on-screen keyboard 406 such that, e.g., the alphanumeric text becomes part of the treatment record 400.

Further, for example, the treatment record 400 may include a print graphical area 408, which, upon selection, may initiate printing of the treatment record 400 using, e.g., a printer electronically connected, or operatively coupled, to the blood treatment system (e.g., through a data network, etc.). Still further, for example, the treatment record 400 may include a transfer graphical area 410, which, upon selection, may initiate the transfer (e.g., electronic transfer) of the treatment record 400 to another device (such as, e.g., a centralized treatment record server for a clinic or system) over a data network, etc. and/or using a portable memory device (e.g., a USB memory device).

The treatment record 400 may be deleted in response to some of the actions performed using the graphical user interface 200 such as printing or transferring. For example, after the treatment record 400 has been printed by the user selecting the print graphical area 408 or transferred to another device by the user selecting the transfer graphical area 410, the treatment record 400 (e.g., the data making up the treatment record on the system, the displayed treatment record 400 itself, etc.) may be deleted. In other words, the treatment record 400 may be "scrubbed" or removed from the blood treatment system after the treatment record 400 has been reproduced elsewhere through printing or digital transfer. Thus, the next user of the blood treatment system may not be able to access the previous treatment records generated by the system to, e.g., provide patient privacy.

Still further, for example, the treatment record 400 may include a sign graphical area 412, which, upon selection, may initiate the display of a signature block, or dialog, configured for entry of a digital signature of a user to, e.g., confirm the contents of the treatment record 400. In at least one embodiment, the signature block may include an on-screen entry box for a user to trace a signature using their finger. In at least one embodiment, the signature block may include an on-screen keyboard similar to the on-screen keyboard 406 depicted in FIG. 8 for entry of a digital signature such as, e.g., "/Markus Johnson/" into the signature block. Upon entry of the signature into the signature block, the signature may become part of the treatment record 400, and thus, printed on and/or transferred with the treatment record 400.

In one or more embodiments, the treatment record 400 may not be removed from the operations region 202 of the graphical user interface 200 without a user performing one or more of the various actions described herein. For example, before the treatment record 400 may be removed from the operations region 202, a user may be required to electronically sign the treatment record 400. Further, for example, before the treatment record 400 may be removed from the operations region 202, a user may be required to print or electronically transfer the treatment record 400. Further, more than one action may be required for the removal of the treatment record 400 from the operations region 202 of the graphical user interface 200. For instance, before the treatment record 400 may be removed from the operations region 202, a user may be required to electronically sign the treatment record 400 and either print or electronically transfer the treatment record 400.

Further, in one or more embodiments, the treatment record 400 may be removed from the operations region 202 of the graphical user interface 200 without a user performing one or more of the various actions described herein. Instead, a user may choose to disregard the treatment record 400 by selecting a close graphical element 430 or selected an area of the operations region 202 outside of the treatment record 400. Thus, the treatment record 400 may be removed from the operations region 202 of the graphical user interface 200 in response to a user selecting a close graphical element 430 or selecting an area of the operations region 202 outside of the treatment record 400.

Still further, upon the selection of the close graphical element 430 or the operations region 202 outside of the treatment record 400, the treatment record 400 may be deleted or removed from the blood treatment system. In at least one embodiment, a confirmation dialog may be displayed in the operations region 202 of the graphical user interface 200 in response to a user disregarding the treatment record 400 that asks the user whether the user would like to delete the treatment record 400 or confirms with the user that, by disregarding the treatment record 400, the treatment record 400 will be deleted from the system.

In one or more embodiments, the treatment record 400 may be deleted from the blood treatment system after a selected period of time has elapsed from when the treatment record 400 has been displayed on the graphical user interface 200 and/or the user disregarded the treatment record 400. The selected period of time may be between about 1 minutes and 30 minutes. For example, the selected period of time may be greater than or equal to about 1 minute, greater than or equal to about 5 minutes, greater than or equal to about 10 minutes, greater than or equal to about 15 minutes, greater than or equal to about 30 minutes, etc. Further, for example, the selected period of time may be less than or equal to about 5 hours, less than or equal to about 1 hour, less than or equal to about 45 minutes, less than or equal to about 20 minutes, less than or equal to about 12 minutes, less than or equal to about 7 minutes, less than or equal to about 3 minutes, etc. In other words, the treatment records may have an expiration time.

The treatment record 400 may further include various information with respect to one or more disposable elements used by the blood treatment system. For example, a user may enter disposable element information including information such as, e.g., a disposable element lot number, expiration date of disposable element, brand name of disposable element, and/or any additional information regarding the type of disposable element (e.g., brand name) into the blood treatment system such that the disposable element information becomes part of the treatment record 400. In one or more embodiments, the system may include a barcode scanner, and a user may enter disposable element information by scanning a barcode on the disposable element using the barcode scanner.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the systems and methods described herein. Various modifications of the illustrative embodiments, as well as additional embodiments of the disclosure, will be apparent upon reference to this description.

What is claimed is:

1. An extracorporeal blood treatment system comprising:
an extracorporeal blood treatment apparatus comprising one or more pumps, one or more sensors, and one or more disposable elements for use in a plurality of different extracorporeal blood treatment modalities;
a display comprising a graphical user interface, wherein the graphical user interface is configured to display treatment records for an extracorporeal blood treatment; and
a computing apparatus comprising one or more processors, wherein the computing apparatus is operatively coupled to the extracorporeal blood treatment apparatus and the display, wherein the computing apparatus is configured to:
select an extracorporeal blood treatment modality from the plurality of different extracorporeal blood treatment modalities in response to the user using the graphical user interface,
perform the extracorporeal blood treatment according to the selected extracorporeal blood treatment modality for a patient using the extracorporeal blood treatment apparatus,
monitor a plurality of parameters using the extracorporeal blood treatment apparatus during the extracorporeal blood treatment,
generate a treatment record comprising:
patient and treatment information,
the selected extracorporeal blood treatment modality,
a plurality of values for a compulsory set of the plurality of parameters monitored during the selected extracorporeal blood treatment, wherein the compulsory set of the plurality of parameters are not set by a user,
a plurality of values for a dependent set of the plurality of parameters monitored during the selected extracorporeal blood treatment, wherein the dependent set of the plurality of parameters are selected in response to at least the selection of the extracorporeal blood treatment modality from the plurality of different extracorporeal blood treatment modalities, and
a plurality of values for a discretionary set of the plurality of parameters monitored during the extracorporeal blood treatment, wherein the discretionary set of the plurality of parameters are selectable by a user, display the treatment record on the graphical user interface in response to the end of the extracorporeal blood treatment, allow a user to disregard the displayed treatment record, and delete the treatment record in response to the user disregarding the displayed treatment record after a selected time period elapses.

2. The system of claim 1, wherein the treatment record further comprises a selectable print graphical area, wherein the computing apparatus is further configured to:

allow a user to select the selectable print graphical area to print the treatment record using a printer; and delete the treatment record in response to the user selecting the selectable print graphical area to print the treatment record using a printer.

3. The system of claim 1, wherein the treatment record further comprises a selectable transfer graphical area, wherein the computing apparatus is further configured to:

allow a user to select the selectable transfer graphical area to transfer the treatment record to another device; and delete the treatment record in response to the user selecting the selectable transfer graphical area to transfer the treatment record to another device.

4. The system of claim 1, wherein the plurality of parameters are monitored periodically using the extracorporeal blood treatment apparatus during the extracorporeal blood treatment, wherein the plurality of values of the compulsory set of the plurality of parameters, the plurality of values of the dependent set of the plurality of parameters, and the plurality of values of the discretionary set of the plurality of parameters are numerically depicted in the treatment record.

5. The system of claim 1, wherein the dependent set of the plurality of parameters are selected in response to at least the configuration of the extracorporeal blood treatment system.

6. The system of claim 1, wherein the plurality of different extracorporeal blood treatment modalities comprises at least two of hemodialysis, hemodiafiltration predilution, hemodiafiltration postdilution, and hemofiltration.

7. The system of claim 1, wherein the patient and treatment information comprises one or more of:

patient name;
patient identifier;
system identifier; and
clinic name.

8. The system of claim 1, wherein the compulsory set of the plurality of parameters comprises one or more of:

blood flow rate;
accumulated blood flow rate;
venous pressure;
arterial pressure;
accumulated ultrafiltration volume;
dialysate flow rate;
dialysate sodium concentration; and
dialysate bicarbonate concentration.

9. The system of claim 1, wherein the dependent set of the plurality of parameters comprises one or more of:

systolic blood pressure;
diastolic blood pressure;
pressure pulse;
accumulated heparin volume;
dialyzer clearance of urea;
dialyzer clearance of urea multiplied by time divided by volume of distribution of urea (KT/V);
dialyzer clearance of urea multiplied by time (KT);
relative blood volume percentage;
convective volume; and
convective clearance rate.

10. The system of claim 9, wherein the convective volume and the convective clearance rate are selected to be within the dependent set of the plurality of parameters in response to the selection of hemofiltration or hemodiafiltration from the plurality of different extracorporeal blood treatment modalities.

11. The system of claim 9, wherein the accumulated heparin volume is selected to be within the dependent set of the plurality of parameters in response to the configuration of the extracorporeal blood treatment apparatus.

12. The system of claim 1, wherein the discretionary set of the plurality of parameters comprises one or more of:

transmembrane pressure;
conductivity;
plasma conductivity;
total set ultrafiltration volume; and
temperature.

13. The system of claim 1, wherein the treatment record further comprises a treatment summary, wherein the treatment summary comprises one or more of:

treatment date;
treatment start time;
treatment type;
access type; and
treatment duration.

14. The system of claim 1, wherein the treatment record further comprises a signature block to receive a signature of a user, and wherein the computing apparatus is further configured to allow a user to sign the signature block displayed on the graphical user interface.

15. The system of claim 1, wherein the treatment record further comprises a notes region to receive notes from a user, and wherein the computing apparatus is further configured to allow a user to add alphanumeric text to the notes region of treatment record displayed on the graphical user interface.

16. The system of claim 1, wherein the computing apparatus is further configured to allow a user to enter disposable element information for each of the one or more disposable elements of the extracorporeal blood treatment apparatus, wherein the disposable element information comprises a disposable element lot number, wherein the treatment record further comprises the disposable element information.

17. The system of claim 16, wherein the computing apparatus further comprises a barcode scanner, wherein allowing a user to enter disposable element information comprising scanning a barcode on the one or more disposable elements using the barcode scanner.

18. The system of claim 1, wherein the display comprises a touchscreen.

19. A method for an extracorporeal blood treatment system comprising:

providing extracorporeal blood treatment apparatus comprising one or more pumps, one or more sensors, and one or more disposable elements for use in performing an extracorporeal blood treatment;

selecting an extracorporeal blood treatment modality from a plurality of different extracorporeal blood treatment modalities, performing the extracorporeal blood treatment according to the selected extracorporeal blood treatment modality for a patient using the extracorporeal blood treatment apparatus;

monitoring a plurality of parameters using the extracorporeal blood treatment apparatus during the extracorporeal blood treatment;
generating a treatment record comprising:
patient and treatment information,
the selected extracorporeal blood treatment modality,
a plurality of values for a compulsory set of the plurality of parameters monitored during the selected extracorporeal blood treatment, wherein the compulsory set of the plurality of parameters are not set by a user,
a plurality of values for a dependent set of the plurality of parameters monitored during the selected extracorporeal blood treatment, wherein the dependent set of the plurality of parameters are selected in response to at least the selection of the extracorporeal blood treatment modality from the plurality of different extracorporeal blood treatment modalities, and
a plurality of values for a discretionary set of the plurality of parameters monitored during the extracorporeal blood treatment, wherein the discretionary set of the plurality of parameters are selectable by a user; and
displaying the treatment record on a graphical user interface in response to the end of the extracorporeal blood treatment,
wherein the method comprises one or more of:
allowing a user to disregard the displayed treatment record and deleting the treatment record in response to the user disregarding the displayed treatment record after a selected time period elapses;
allowing a user to select a selectable print graphical area of the treatment record to print the treatment record using a printer and deleting the treatment record in response to the user selecting the selectable print graphical area to print the treatment record using a printer; and
allowing a user to select a selectable transfer graphical area of the treatment record to transfer the treatment record to another device and deleting the treatment record in response to the user selecting the selectable transfer graphical area to transfer the treatment record to another device.

20. The method of claim 19, wherein the plurality of parameters are monitored periodically using the extracorporeal blood treatment apparatus during the extracorporeal blood treatment, wherein the plurality of values of the compulsory set of the plurality of parameters, the plurality of values of the dependent set of the plurality of parameters, and the plurality of values of the discretionary set of the plurality of parameters are numerically depicted in the treatment record.

21. The method of claim 19, wherein the dependent set of the plurality of parameters are selected in response to at least the configuration of the extracorporeal blood treatment system.

22. The method of claim 19, wherein the plurality of different extracorporeal blood treatment modalities comprises at least two of hemodialysis, hemodiafiltration predilution, hemodiafiltration postdilution, and hemofiltration.

23. The method of claim 19, wherein the patient and treatment information comprises one or more of:
patient name;
patient identifier;
system identifier; and
clinic name.

24. The method of claim 19, wherein the compulsory set of the plurality of parameters comprises one or more of:
blood flow rate;
accumulated blood flow rate;
venous pressure;
arterial pressure;
accumulated ultrafiltration volume;
dialysate flow rate;
dialysate sodium concentration; and
dialysate bicarbonate concentration.

25. The method of claim 19, wherein the dependent set of the plurality of parameters comprises one or more of:
systolic blood pressure;
diastolic blood pressure;
pressure pulse;
accumulated heparin volume;
dialyzer clearance of urea;
dialyzer clearance of urea multiplied by time divided by volume of distribution of urea (KT/V);
dialyzer clearance of urea multiplied by time (KT);
relative blood volume percentage;
convective volume; and
convective clearance rate.

26. The method of claim 19, wherein the dependent set of the plurality of parameters comprises convective volume and convective clearance rate, wherein the convective volume and the convective clearance rate are selected to be within the dependent set of the plurality of parameters in response to the selection of hemofiltration or hemodiafiltration from the plurality of different extracorporeal blood treatment modalities.

27. The method of claim 19, wherein the dependent set of the plurality of parameters comprises accumulated heparin volume, wherein the accumulated heparin volume is selected to be within the dependent set of the plurality of parameters in response to the configuration of the extracorporeal blood treatment apparatus.

28. The method of claim 19, wherein the discretionary set of the plurality of parameters comprises one or more of:
transmembrane pressure;
conductivity;
plasma conductivity;
total set ultrafiltration volume; and
temperature.

29. The method of claim 19, wherein the treatment record further comprises a treatment summary, wherein the treatment summary comprises one or more of:
treatment date;
treatment start time;
treatment type;
access type; and
treatment duration.

30. The method of claim 19, wherein the treatment record further comprises a signature block to receive a signature of a user, and wherein the method further comprises allowing a user to sign the signature block displayed on the graphical user interface.

31. The method of claim 19, wherein the treatment record further comprises a notes region to receive notes from a user, and wherein the method further comprises allowing a user to add alphanumeric text to the notes region of treatment record displayed on the graphical user interface.

32. The method of claim 19, wherein the method further comprises allowing a user to enter disposable element information for each of the one or more disposable elements of the extracorporeal blood treatment apparatus, wherein the disposable element information comprises a disposable element lot number, wherein the treatment record further comprises the disposable element information.

33. The method of claim 32, wherein allowing a user to enter disposable element information comprising scanning a barcode on the one or more disposable elements using a scanner.

34. An extracorporeal blood treatment system comprising:
an extracorporeal blood treatment apparatus comprising one or more pumps, one or more sensors, and one or more disposable elements for use in a plurality of different extracorporeal blood treatment modalities;
a display comprising a graphical user interface, wherein the graphical user interface is configured to display treatment records for an extracorporeal blood treatment; and
a computing apparatus comprising one or more processors, wherein the computing apparatus is operatively coupled to the extracorporeal blood treatment apparatus and the display, wherein the computing apparatus is configured to:
select an extracorporeal blood treatment modality from the plurality of different extracorporeal blood treatment modalities in response to the user using the graphical user interface,
perform the extracorporeal blood treatment according to the selected extracorporeal blood treatment modality for a patient using the extracorporeal blood treatment apparatus,
monitor a plurality of parameters using the extracorporeal blood treatment apparatus during the extracorporeal blood treatment,
generate a treatment record comprising:
patient and treatment information,
the selected extracorporeal blood treatment modality,
a plurality of values for a compulsory set of the plurality of parameters monitored during the selected extracorporeal blood treatment, wherein the compulsory set of the plurality of parameters are not set by a user,
a plurality of values for a dependent set of the plurality of parameters monitored during the selected extracorporeal blood treatment, wherein the dependent set of the plurality of parameters are selected in response to at least the selection of the extracorporeal blood treatment modality from the plurality of different extracorporeal blood treatment modalities,
a plurality of values for a discretionary set of the plurality of parameters monitored during the extracorporeal blood treatment, wherein the discretionary set of the plurality of parameters are selectable by a user, and
a selectable print graphical area,
display the treatment record on the graphical user interface in response to the end of the extracorporeal blood treatment,
allow a user to select the selectable print graphical area to print the treatment record using a printer, and
delete the treatment record in response to the user selecting the selectable print graphical area to print the treatment record using a printer.

35. The system of claim 34, wherein the computing apparatus is further configured to:
allow a user to disregard the displayed treatment record; and
delete the treatment record in response to the user disregarding the displayed treatment record after a selected time period elapses.

36. The system of claim 34, wherein the treatment record further comprises a selectable transfer graphical area, wherein the computing apparatus is further configured to:
allow a user to select the selectable transfer graphical area to transfer the treatment record to another device; and
delete the treatment record in response to the user selecting the selectable transfer graphical area to transfer the treatment record to another device.

37. The system of claim 34, wherein the plurality of parameters are monitored periodically using the extracorporeal blood treatment apparatus during the extracorporeal blood treatment, wherein the plurality of values of the compulsory set of the plurality of parameters, the plurality of values of the dependent set of the plurality of parameters, and the plurality of values of the discretionary set of the plurality of parameters are numerically depicted in the treatment record.

38. The system of claim 34, wherein the dependent set of the plurality of parameters are selected in response to at least the configuration of the extracorporeal blood treatment system.

39. The system of claim 34, wherein the plurality of different extracorporeal blood treatment modalities comprises at least two of hemodialysis, hemodiafiltration predilution, hemodiafiltration postdilution, and hemofiltration.

40. The system of claim 34, wherein the patient and treatment information comprises one or more of:
patient name;
patient identifier;
system identifier; and
clinic name.

41. The system of claim 34, wherein the compulsory set of the plurality of parameters comprises one or more of:
blood flow rate;
accumulated blood flow rate;
venous pressure;
arterial pressure;
accumulated ultrafiltration volume;
dialysate flow rate;
dialysate sodium concentration; and
dialysate bicarbonate concentration.

42. The system of claim 34, wherein the dependent set of the plurality of parameters comprises one or more of:
systolic blood pressure;
diastolic blood pressure;
pressure pulse;
accumulated heparin volume;
dialyzer clearance of urea;
dialyzer clearance of urea multiplied by time divided by volume of distribution of urea (KT/V);
dialyzer clearance of urea multiplied by time (KT);
relative blood volume percentage;
convective volume; and
convective clearance rate.

43. The system of claim 42, wherein the convective volume and the convective clearance rate are selected to be within the dependent set of the plurality of parameters in response to the selection of hemofiltration or hemodiafiltration from the plurality of different extracorporeal blood treatment modalities.

44. The system of claim 42, wherein the accumulated heparin volume is selected to be within the dependent set of the plurality of parameters in response to the configuration of the extracorporeal blood treatment apparatus.

45. The system of claim 34, wherein the discretionary set of the plurality of parameters comprises one or more of:
   transmembrane pressure;
   conductivity;
   plasma conductivity;
   total set ultrafiltration volume; and
   temperature.

46. The system of claim 34, wherein the treatment record further comprises a treatment summary, wherein the treatment summary comprises one or more of:
   treatment date;
   treatment start time;
   treatment type;
   access type; and
   treatment duration.

47. The system of claim 34, wherein the treatment record further comprises a signature block to receive a signature of a user, and wherein the computing apparatus is further configured to allow a user to sign the signature block displayed on the graphical user interface.

48. The system of claim 34, wherein the treatment record further comprises a notes region to receive notes from a user, and wherein the computing apparatus is further configured to allow a user to add alphanumeric text to the notes region of treatment record displayed on the graphical user interface.

49. The system of claim 34, wherein the computing apparatus is further configured to allow a user to enter disposable element information for each of the one or more disposable elements of the extracorporeal blood treatment apparatus, wherein the disposable element information comprises a disposable element lot number, wherein the treatment record further comprises the disposable element information.

50. The system of claim 49, wherein the computing apparatus further comprises a barcode scanner, wherein allowing a user to enter disposable element information comprising scanning a barcode on the one or more disposable elements using the barcode scanner.

51. The system of claim 34, wherein the display comprises a touchscreen.

52. An extracorporeal blood treatment system comprising:
   an extracorporeal blood treatment apparatus comprising one or more pumps, one or more sensors, and one or more disposable elements for use in a plurality of different extracorporeal blood treatment modalities;
   a display comprising a graphical user interface, wherein the graphical user interface is configured to display treatment records for an extracorporeal blood treatment; and
   a computing apparatus comprising one or more processors, wherein the computing apparatus is operatively coupled to the extracorporeal blood treatment apparatus and the display, wherein the computing apparatus is configured to:
      select an extracorporeal blood treatment modality from the plurality of different extracorporeal blood treatment modalities in response to the user using the graphical user interface,
      perform the extracorporeal blood treatment according to the selected extracorporeal blood treatment modality for a patient using the extracorporeal blood treatment apparatus,
      monitor a plurality of parameters using the extracorporeal blood treatment apparatus during the extracorporeal blood treatment,
      generate a treatment record comprising:
         patient and treatment information,
         the selected extracorporeal blood treatment modality,
         a plurality of values for a compulsory set of the plurality of parameters monitored during the selected extracorporeal blood treatment, wherein the compulsory set of the plurality of parameters are not set by a user,
         a plurality of values for a dependent set of the plurality of parameters monitored during the selected extracorporeal blood treatment, wherein the dependent set of the plurality of parameters are selected in response to at least the selection of the extracorporeal blood treatment modality from the plurality of different extracorporeal blood treatment modalities,
         a plurality of values for a discretionary set of the plurality of parameters monitored during the extracorporeal blood treatment, wherein the discretionary set of the plurality of parameters are selectable by a user, and
         a selectable transfer graphical area,
      display the treatment record on the graphical user interface in response to the end of the extracorporeal blood treatment,
      allow a user to select the selectable transfer graphical area to transfer the treatment record to another device, and
      delete the treatment record in response to the user selecting the selectable transfer graphical area to transfer the treatment record to another device.

53. The system of claim 52, wherein the computing apparatus is further configured to:
   allow a user to disregard the displayed treatment record; and
   delete the treatment record in response to the user disregarding the displayed treatment record after a selected time period elapses.

54. The system of claim 52, wherein the treatment record further comprises a selectable print graphical area, wherein the computing apparatus is further configured to:
   allow a user to select the selectable print graphical area to print the treatment record using a printer; and
   delete the treatment record in response to the user selecting the selectable print graphical area to print the treatment record using a printer.

55. The system of claim 52, wherein the plurality of parameters are monitored periodically using the extracorporeal blood treatment apparatus during the extracorporeal blood treatment, wherein the plurality of values of the compulsory set of the plurality of parameters, the plurality of values of the dependent set of the plurality of parameters, and the plurality of values of the discretionary set of the plurality of parameters are numerically depicted in the treatment record.

56. The system of claim 52, wherein the dependent set of the plurality of parameters are selected in response to at least the configuration of the extracorporeal blood treatment system.

57. The system of claim 52, wherein the plurality of different extracorporeal blood treatment modalities comprises at least two of hemodialysis, hemodiafiltration predilution, hemodiafiltration postdilution, and hemofiltration.

58. The system of claim 52, wherein the patient and treatment information comprises one or more of:
   patient name;
   patient identifier;
   system identifier; and
   clinic name.

59. The system of claim 52, wherein the compulsory set of the plurality of parameters comprises one or more of:
- blood flow rate;
- accumulated blood flow rate;
- venous pressure;
- arterial pressure;
- accumulated ultrafiltration volume;
- dialysate flow rate;
- dialysate sodium concentration; and
- dialysate bicarbonate concentration.

60. The system of claim 52, wherein the dependent set of the plurality of parameters comprises one or more of:
- systolic blood pressure;
- diastolic blood pressure;
- pressure pulse;
- accumulated heparin volume;
- dialyzer clearance of urea;
- dialyzer clearance of urea multiplied by time divided by volume of distribution of urea (KT/V);
- dialyzer clearance of urea multiplied by time (KT);
- relative blood volume percentage;
- convective volume; and
- convective clearance rate.

61. The system of claim 60, wherein the convective volume and the convective clearance rate are selected to be within the dependent set of the plurality of parameters in response to the selection of hemofiltration or hemodiafiltration from the plurality of different extracorporeal blood treatment modalities.

62. The system of claim 60, wherein the accumulated heparin volume is selected to be within the dependent set of the plurality of parameters in response to the configuration of the extracorporeal blood treatment apparatus.

63. The system of claim 52, wherein the discretionary set of the plurality of parameters comprises one or more of:
- transmembrane pressure;
- conductivity;
- plasma conductivity;
- total set ultrafiltration volume; and
- temperature.

64. The system of claim 52, wherein the treatment record further comprises a treatment summary, wherein the treatment summary comprises one or more of:
- treatment date;
- treatment start time;
- treatment type;
- access type; and
- treatment duration.

65. The system of claim 52, wherein the treatment record further comprises a signature block to receive a signature of a user, and wherein the computing apparatus is further configured to allow a user to sign the signature block displayed on the graphical user interface.

66. The system of claim 52, wherein the treatment record further comprises a notes region to receive notes from a user, and wherein the computing apparatus is further configured to allow a user to add alphanumeric text to the notes region of treatment record displayed on the graphical user interface.

67. The system of claim 52, wherein the computing apparatus is further configured to allow a user to enter disposable element information for each of the one or more disposable elements of the extracorporeal blood treatment apparatus, wherein the disposable element information comprises a disposable element lot number, wherein the treatment record further comprises the disposable element information.

68. The system of claim 67, wherein the computing apparatus further comprises a barcode scanner, wherein allowing a user to enter disposable element information comprising scanning a barcode on the one or more disposable elements using the barcode scanner.

69. The system of claim 52, wherein the display comprises a touchscreen.

* * * * *